US012778033B2

(12) United States Patent
Liu et al.

(10) Patent No.: US 12,778,033 B2
(45) Date of Patent: Nov. 3, 2026

(54) **METHOD USING *STRATIOLAELAPS SCIMITUS* DURING FLOAT-TRAY-BASED TOBACCO SEEDLING CULTIVATION**

(71) Applicant: Yunnan Tobacco Co., Ltd. Kunming Branch, Kunming (CN)

(72) Inventors: Zhengling Liu, Kunming (CN); Yonghui Xie, Kunming (CN); DeKai Ning, Kunming (CN); Hongming Li, Kunming (CN); Youguo Zhan, Kunming (CN); Xiaofei Gu, Kunming (CN); Zhijiang Wang, Kunming (CN); Dingguo Shi, Kunming (CN); Daquan Yang, Kunming (CN); Facong Qian, Kunming (CN); Endong Wang, Kunming (CN); Bo Zhang, Kunming (CN); Xuenong Xu, Kunming (CN)

(73) Assignee: Yunnan Tobacco Co., Ltd. Kunming Branch, Kunming (CN)

( * ) Notice: Subject to any disclaimer, the term of this patent is extended or adjusted under 35 U.S.C. 154(b) by 0 days.

(21) Appl. No.: 19/286,074

(22) Filed: Jul. 30, 2025

(65) Prior Publication Data

US 2026/0144197 A1 May 28, 2026

(30) Foreign Application Priority Data

Nov. 27, 2024 (CN) ........................ 202411716652.5

(51) Int. Cl.
*A01G 22/45* (2018.01)
*A01G 13/10* (2006.01)
(Continued)

(52) U.S. Cl.
CPC ........... *A01G 22/45* (2018.02); *A01G 13/105* (2013.01); *A01G 31/024* (2025.01); *A01K 67/31* (2025.01)

(58) Field of Classification Search
CPC ...... A01G 22/45; A01G 31/024; A01G 31/02; A01G 13/00; A01G 13/10; A01G 13/105; A01K 67/31
See application file for complete search history.

(56) References Cited

U.S. PATENT DOCUMENTS

| | | | | |
|---|---|---|---|---|
| 2009/0205057 A1* | 8/2009 | Bolckmans | A01K 67/30 | 800/8 |
| 2019/0307082 A1* | 10/2019 | Parker | A01G 24/25 | |
| 2023/0029171 A1* | 1/2023 | Lewis | A24B 13/00 | |

FOREIGN PATENT DOCUMENTS

| | | | | |
|---|---|---|---|---|
| CN | 207355017 U | 5/2018 | | |
| CN | 108122025 A * | 6/2018 | | A01K 67/30 |

(Continued)

*Primary Examiner* — Magdalena Topolski
*Assistant Examiner* — Spencer T Callaway
(74) *Attorney, Agent, or Firm* — Nitin Kaushik

(57) ABSTRACT

A method for controlling thrips using *Stratiolaelaps scimitus* during float-tray-based tobacco seedling cultivation, including the following steps: 1) arranging a seedbed in a wind-sheltered sunny area with upwind positioning, and removing host plants of the thrips around the seedbed; 2) sowing 2 tobacco seeds per cell in float trays for the float-tray-based tobacco seedling cultivation, arranging 32 float trays per nursery greenhouse, placing the float trays in a nutrient solution tank, adding a formulated fertilizer solution for the float-tray-based tobacco seedling cultivation into the nutrient solution tank, arranging a plurality of nursery greenhouses in close proximity to form a nursery greenhouse cluster, erecting a plastic film vertically around the nursery greenhouse cluster, and arranging an insect-proof net around the nursery greenhouse cluster; and 3) after a rate of seedling emergence reaches over 90%, thinning seedlings.

10 Claims, 1 Drawing Sheet

(51) Int. Cl.
*A01G 31/02* (2006.01)
*A01K 67/31* (2025.01)

(56) References Cited

FOREIGN PATENT DOCUMENTS

| | | | | | |
|---|---|---|---|---|---|
| CN | 108450208 | A | * | 8/2018 | ............. A01G 13/00 |
| CN | 109496762 | A | | 3/2019 | |
| CN | 116649301 | A | | 8/2023 | |
| CN | 116998469 | A | | 11/2023 | |

* cited by examiner

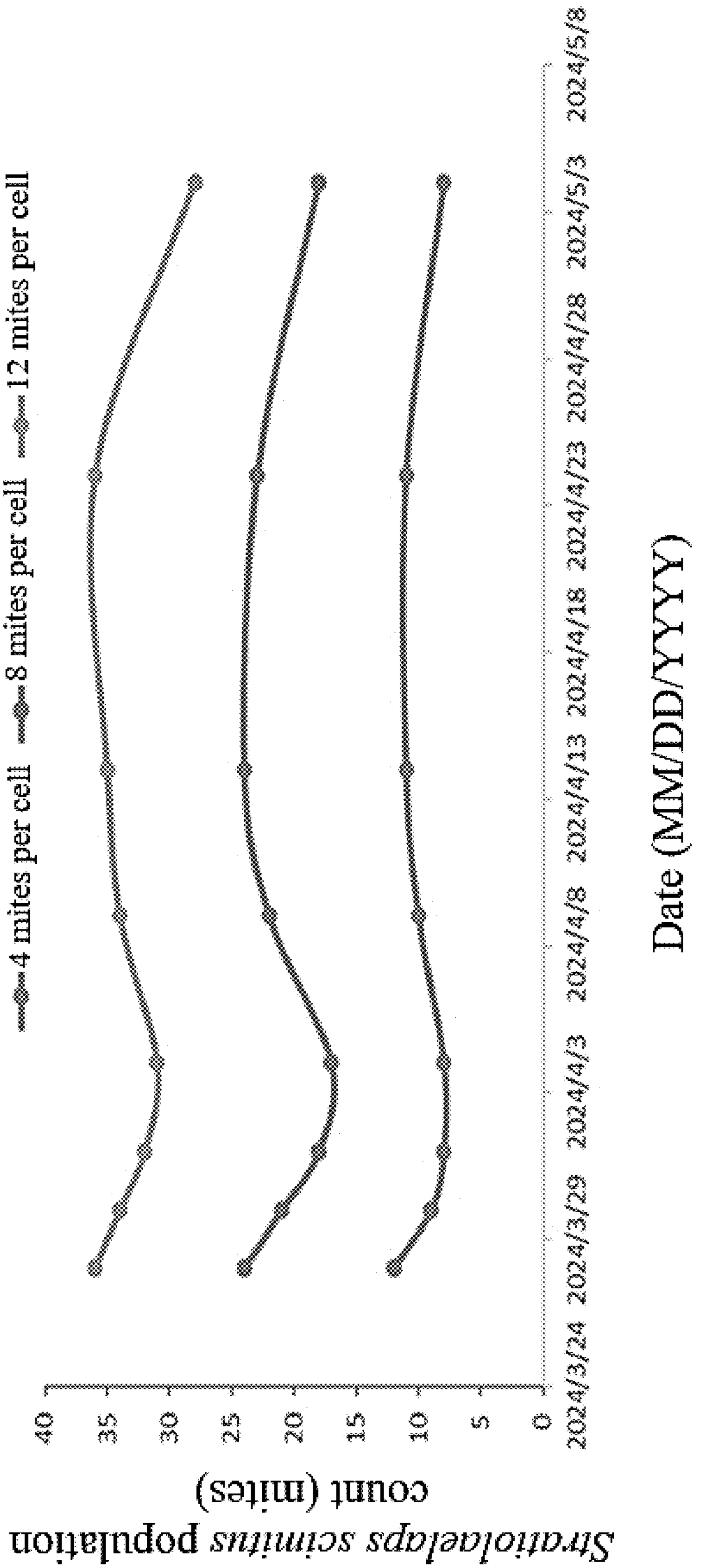
4 mites per cell
8 mites per cell
12 mites per cell
*Stratiolaelaps scimitus* population count (mites)
0
5
10
15
20
25
30
35
40
2024/3/24
2024/3/29
2024/4/3
2024/4/8
2024/4/13
2024/4/18
2024/4/23
2024/4/28
2024/5/3
2024/5/8
Date (MM/DD/YYYY)

METHOD USING *STRATIOLAELAPS SCIMITUS* DURING FLOAT-TRAY-BASED TOBACCO SEEDLING CULTIVATION

CROSS-REFERENCE TO RELATED APPLICATIONS

The application claims priority to Chinese patent application No. 2024117166525, filed on Nov. 27, 2024, the entire contents of which are incorporated herein by reference.

TECHNICAL FIELD

The present application relates to the technical field of tobacco seedling cultivation, and in particular, to a method for controlling thrips using *Stratiolaelaps scimitus* during float-tray-based tobacco seedling cultivation.

BACKGROUND

The healthy growth of tobacco seedlings is of significant importance for the later-stage prevention and control of pests and diseases, as well as for ensuring high-quality and stable tobacco leaf production. During the seedling cultivation stage, tobacco plants are susceptible to damage by thrips, making this stage both the main and optimal stage for thrips control (CN201811375808.2). Western flower thrips and *Thrips tabaci* are two primary thrips species that infest tobacco plants, and these thrips also serve as major viral vectors, posing a serious threat to the tobacco industry.

A tobacco seedling cultivation method primarily employs float-tray cultivation, where a plurality of nutrient solution tanks are arranged in a nursery greenhouse, with a plurality of foam boards floating in the tanks. The foam boards are provided with a plurality of recesses to accommodate tobacco seedlings and their root substrate. The float trays float directly on the nutrient solution in the tanks, supplying nutrients and water required for seed germination and growth through capillary action and transpiration of the substrate. This seedling cultivation method offers the advantages of occupying a small area, high seedling cultivation efficiency, minimal substrate usage, reduced exposed substrate area for diminishing survival space for soil-borne pests and diseases, and a high seedling survival rate.

To prevent the tobacco seedlings from pest infestation, an insect-proof net is typically used in the nursery greenhouses. However, due to the mesh size restrictions of conventional insect-proof nets, they can only exclude large pests such as aphids and whiteflies while proving ineffective against small thrips. Furthermore, if insect-proof nets with an excessively small mesh size are used, it is difficult to ensure ventilation and air circulation within the nursery greenhouses and above the seedbeds, ultimately resulting in diminished seedling quality and reduced survival rates.

With growing concerns regarding smoking safety, biological control methods have been increasingly adopted for thrips control during tobacco seedling cultivation, especially employing predatory mites to prey upon thrips (i.e., mite-mediated pest control, as disclosed in CN201720932761.X). This method also provides source control for both thrips and their transmitted Tomato spotted wilt virus. For example, CN201811375808.2 discloses a method for controlling thrips during tobacco seedling cultivation, which utilizes *Amblyseius cucumeris* as the predatory mite. This method demonstrates a population reduction rate of 54.44% and achieves control efficacy of 70.24% against thrips during the seedling cultivation stage.

*Stratiolaelaps scimitus* is a fast-moving mite species inhabiting the soil surface, which is utilized for controlling various pests including fungus gnat larvae, thrips, springtails, *Tyrophagus putrescentiae*, and nematodes in crops such as vegetables, ornamental plants, and edible fungi.

An existing method for controlling thrips using *Stratiolaelaps scimitus* in the prior art includes: monitoring pest populations through sticky traps or visual inspection 7-10 days after crop transplantation, followed by release of *Stratiolaelaps scimitus* upon detection of thrips. Biological control is mainly implemented by releasing *Stratiolaelaps scimitus* onto plant roots at a dosage of 100-200 mites/$m^2$, concurrently with foliar release of *Neoseiulus barkeri* or *Neoseiulus cucumeris* at a dosage of 100-200 mites/$m^2$. This release protocol is repeated once every 2 weeks for 2-3 consecutive times to enhance control efficacy.

The rearing and application conditions for *Stratiolaelaps scimitus* require a temperature of 18-30° C. and a relative humidity of 65-95% to ensure optimal activity and efficacy.

As described above, the existing application of *Stratiolaelaps scimitus* is mainly used for thrips control in transplanted plants, which does not inherently adapt to thrips control in non-transplanted tobacco seedlings during float-tray-based tobacco seedling cultivation. Furthermore, existing release methods for *Stratiolaelaps scimitus* typically require concurrent application with other mite species to achieve satisfactory control efficacy, as the sole use of *Stratiolaelaps scimitus* proves insufficient for effective pest control. In addition, research indicates that *Stratiolaelaps scimitus* requires soil habitation to prey upon mature larvae and pupae of western flower thrips that descend into soil for pupation. The short cultivation period and small exposed soil surface area for float-tray-based tobacco seedling cultivation present challenges in ensuring timely soil penetration by *Stratiolaelaps scimitus* released by the existing release methods, thereby compromising its efficacy in timely eliminating the mature larvae and pupae of various thrips species.

The information disclosed in the background is merely intended to enhance understanding of the overall background of the present invention and shall not be construed as admitting or suggesting in any form that such information constitutes the prior art already known to a person of ordinary skill in the art.

SUMMARY

The present application provides a method for controlling thrips using *Stratiolaelaps scimitus* during float-tray-based tobacco seedling cultivation to address the technical problem existing in the prior art that it is difficult to control various developmental stages of thrips in tobacco seedlings during float-tray-based tobacco seedling cultivation.

The present application provides a method for controlling thrips using *Stratiolaelaps scimitus* during float-tray-based tobacco seedling cultivation, including the following steps:

1) arranging a seedbed in a wind-sheltered sunny area with upwind positioning, and removing host plants of the thrips around the seedbed;
2) sowing 2 tobacco seeds per cell in float trays for the float-tray-based tobacco seedling cultivation, arranging 32 float trays per nursery greenhouse, placing the float trays in a nutrient solution tank, adding a formulated fertilizer solution for the float-tray-based tobacco seedling cultivation into the nutrient solution tank, arranging a plurality of nursery greenhouses in close proximity to form a nursery greenhouse cluster, erecting a plastic film vertically around the nursery greenhouse cluster, and arranging an insect-proof net around the nursery greenhouse cluster; and 3) after a rate of seedling emergence reaches over 90%, thinning seedlings, and on the following day, releasing the *Stratiolaelaps scimitus* into root soil of plants in the float trays at a rate of 4-12 mites per cell, followed by standard seedling management until transplanting of the seedlings.

Preferably, the step of thinning the seedlings is performed by retaining only one relatively healthy seedling per cell.

Preferably, the float trays employed in the method each include 162 cells.

Preferably, the step of erecting the plastic film vertically around the nursery greenhouse cluster uses a black or silver-black plastic film, with a bottom of the plastic film abutting against a ground surface.

Preferably, the host plants of the thrips at least include: *Bidens pilosa, Capsicum annuum, Solanum melongena*, and various flowering ornamental plants.

Preferably, a method for performing the step of removing the host plants of the thrips includes manual removal and application of chemical pesticide reagents.

Preferably, the application of chemical pesticide reagents includes spraying at least one of spinetoram solution, imidacloprid solution, and acetamiprid solution at a safe dosage.

Preferably, the step of removing the host plants of the thrips covers an area of at least 50 m around the nursery greenhouse cluster.

Preferably, the step of removing the host plants of the thrips covers an area of 50-100 m around the nursery greenhouse cluster.

Preferably, the step of removing the host plants of the thrips is performed 10 days before the step of sowing the tobacco seeds.

Preferably, a preparation method of the formulated fertilizer solution for the float-tray-based tobacco seedling cultivation includes: adding water into the nutrient solution tank; adding a formulated fertilizer for the float-tray-based tobacco seedling cultivation into the water; and then stirring for complete dissolution.

The present application has the following beneficial effects:

1) the method for controlling thrips using *Stratiolaelaps scimitus* during float-tray-based tobacco seedling cultivation provided by the present application achieves effective control against soil-dwelling and foliar-dwelling thrips as well as thrips in the surrounding environment during float-tray-based tobacco seedling cultivation, demonstrating control efficacy of 50%-80% (66.81% on average) against soil-dwelling developmental stages of thrips including pupae, 30%-60% (50.82% on average) against trap-monitored thrips; and 30%-80% (54.34% on average) against foliar-dwelling thrips through population surveys; and 2) the method for controlling thrips using *Stratiolaelaps scimitus* during float-tray-based tobacco seedling cultivation provided by the present application enables the establishment of *Stratiolaelaps scimitus* populations within the soil on the float trays following mite release, thereby achieving effective thrips control throughout the seedling cultivation period. Notably, the method achieves satisfactory control efficacy by using only *Stratiolaelaps scimitus*, indicating it can effectively enhance thrips control during float-tray-based tobacco seedling cultivation.

BRIEF DESCRIPTION OF THE DRAWINGS

The FIGURE is a line chart of statistical results of *Stratiolaelaps scimitus* population counts in Treatments 1-3 of Example 1 provided in the present application.

DETAILED DESCRIPTION OF THE EMBODIMENTS

The present invention will be further described in detail below with reference to the accompanying drawings and embodiments, but the description shall not be construed in any way as limiting the present invention. Any modifications or improvements made based on the teachings of the present invention shall fall within the protection scope of the present invention.

EXAMPLES

Unless otherwise indicated, all materials and instruments used in the following embodiments were obtained through commercial channels, and all detection methods employed were existing methods in the prior art.

Example 1

Step 1: Selection of Seedbed Location and Control of Thrips in the Surrounding Environment 1) Selection of seedbed location: the seedbed was arranged in a wind-sheltered sunny area with upwind positioning to ensure ventilation and air circulation of the seedbed.

2) Removal of thrips habitats in the surrounding environment: host plants of thrips were removed or treated with pesticides to reduce potential sources of thrips infestation; all host plants of thrips, including *Bidens pilosa, Capsicum annuum, Solanum melongena*, and various flowering ornamental plants, were eradicated within an area of 50-100 m around the seedbed. If any host plants of thrips were present in this area, they were eradicated 10 days before seed sowing; and for plants within an area of 50-100 m around the seedbed, a chemical control treatment targeting thrips was conducted 10 days before tobacco seedling emergence, where a safe application dosage of spinetoram solution as the pesticide for chemical control was employed for spraying. The safe application dosages of all pesticides used in the following embodiments were prepared in accordance with the instructions for use of each pesticide.

3) Ground treatment of seedling cultivation area: a black or silver-black plastic film with a width of more than one meter was erected vertically against the ground surface around the nursery greenhouse cluster composed of nursery greenhouses to enhance pest control efficacy within the nursery greenhouses and mitigate contamination by external thrips populations.

Step 2: Seed Sowing and Seedling Cultivation

1) Seedling cultivation was conducted using 162-cell float trays measuring 35 cm×65 cm, with two tobacco seeds per cell during seed sowing.

2) Following seed sowing in the float trays, nutrient solution tanks within the nursery greenhouses were filled with water to a depth of 7-8 cm, and then each nutrient solution tank received 1000 g of formulated fertilizers for float-tray-based tobacco seedling cultivation, with 32 float trays arranged in each nutrient solution tank. Plastic films were laid on the ground around the nursery greenhouses for thermal insulation, with an unsealed gap of 10-15 cm left at the bottom for ventilation. Shade nets were arranged atop the nursery greenhouses for shading.

3) To prevent pest infestation during seedling cultivation, the openings of all nursery greenhouses were covered with insect-proof nets having a mesh size of over 60, thereby achieving integrated seedling cultivation and pest control.

Step 3: Release of *Stratiolaelaps scimitus*

1) Thinning of seedlings: when the rate of seedling emergence reached over 90% (under natural conditions in Kunming, approximately 10 days were required) after seed sowing, the seedlings were thinned to retain one seedling per cell.

2) Inoculation of *Stratiolaelaps scimitus*: On the following day post-thinning, *Stratiolaelaps scimitus* was released into root soil of plants in the float trays at a rate of 4-12 mites per cell. (The mite inoculation material was prepared according to Example 1 of CN202310743167.6, yielding 5,000 mites per bag, with one bag of mites sufficient for approximately 4 float trays.)

3) Monitoring of *Stratiolaelaps scimitus* and thrips populations: 1 blue sticky trap was suspended above each seedbed to monitor thrips populations, and random sampling of three tobacco seedlings per seedbed was conducted to quantify *Stratiolaelaps scimitus* and thrips pupae populations in the corresponding cells.

The method described in Example 1 was applied to floating tobacco seedbeds in Kunming for thrips control, with 3 *Stratiolaelaps scimitus* release treatments established:

Treatment 1:4 *Stratiolaelaps scimitus* mites per cell;

Treatment 2:8 *Stratiolaelaps scimitus* mites per cell;

Treatment 3:12 *Stratiolaelaps scimitus* mites per cell;

Control group: no *Stratiolaelaps scimitus* was released. Each treatment was repeated 3 times.

On the following day post-thinning when the rate of seedling emergence reached over 90%, *Stratiolaelaps scimitus* was released to the bases of tobacco seedlings in each treatment, followed by population surveys of both *Stratiolaelaps scimitus* and thrips conducted on days 3, 5, 7, 10, 15, 20, 30, and 40 post-release until the tobacco seedlings were ready for transplanting. The populations of thrips and *Stratiolaelaps scimitus* were monitored and surveyed, with mite and thrips counts determined using established methodologies through sampling of 5 g growth substrate per treatment.

The survey results demonstrated that following the release of *Stratiolaelaps scimitus* according to the method provided in the present application, the *Stratiolaelaps scimitus* mites successfully established and maintained stable populations in the soil on the float trays. As shown in the line chart of the FIGURE depicting statistical results of *Stratiolaelaps scimitus* population counts in Treatments 1-3: Treatment 1 maintained a population density of 5-15 mites, Treatment 2 maintained a population density of 15-25 mites, and Treatment 3 maintained a population density of 28-37 mites. All treatments exhibited mite counts exceeding the initial number released, indicating successful population establishment.

The soil-dwelling developmental stages of thrips including pupae in Treatments 1-3 were separately quantified, with the results shown in Table 1.

TABLE 1

Control Efficacy of Releasing *Stratiolaelaps scimitus* against Soil-dwelling Thrips Pupae

| Time | Control: Population reduction rate, % | Release of *Stratiolaelaps scimitus*: Population reduction rate, % | Release of *Stratiolaelaps scimitus*: Control efficacy, % |
|---|---|---|---|
| D 3 | −100.00 | 0.00 | 50.00 |
| D 5 | −200.00 | 0.00 | 66.67 |
| D 7 | −300.00 | 0.00 | 75.00 |
| D 10 | −400.00 | −100.00 | 60.00 |
| D 15 | −600.00 | −100.00 | 71.43 |
| D 20 | −800.00 | −100.00 | 77.78 |
| D 30 | −900.00 | −200.00 | 70.00 |
| D 40 | −1000.00 | −300.00 | 63.64 |
| Average | −537.50 | −100.00 | 66.81 |

Note:

Population reduction rate = 100 × (Initial population density − Later population density)/Initial population density; Control efficacy = 100 × (Treated population reduction rate − Control population reduction rate)/(100 − Control population reduction rate);

for soil-dwelling developmental stages of thrips including pupae, the control efficacy ranged between 50% and 80%, with an average control efficacy of 66.81% (as shown in Table 1).

During sampling surveys, foliar-dwelling and trap-monitored thrips populations were separately surveyed for Treatments 1-3, with the results shown in Tables 2-3.

TABLE 2

Control Efficacy of Releasing *Stratiolaelaps scimitus* against Trap-monitored Thrips

| Time | Control: Population reduction rate, % | Release of *Stratiolaelaps scimitus*: Population reduction rate, % | Release of *Stratiolaelaps scimitus*: Control efficacy, % |
|---|---|---|---|
| D 3 | −50.00 | 0.00 | 33.33 |
| D 5 | −150.00 | 0.00 | 60.00 |
| D 7 | −400.00 | −150.00 | 50.00 |
| D 10 | −500.00 | −200.00 | 50.00 |
| D 15 | −550.00 | −200.00 | 53.85 |
| D 20 | −650.00 | −300.00 | 46.67 |
| D 30 | −900.00 | −350.00 | 55.00 |
| D 40 | −1200.00 | −450.00 | 57.69 |
| Average | −550.00 | −206.25 | 50.82 |

Note:

Population reduction rate = 100 × (Initial population density − Later population density)/Initial population density; Control efficacy = 100 × (Treated population reduction rate − Control population reduction rate)/(100 − Control population reduction rate)

TABLE 3

Control Efficacy of Releasing *Stratiolaelaps scimitus* against Foliar-dwelling Thrips

| Time | Control: Population reduction rate, % | Release of *Stratiolaelaps scimitus*: Population reduction rate, % | Release of *Stratiolaelaps scimitus*: Control efficacy, % |
|---|---|---|---|
| D 3 | 0.00 | 33.33 | 33.33 |
| D 5 | −33.33 | 33.33 | 50.00 |
| D 7 | −66.67 | 0.00 | 40.00 |
| D 10 | −233.33 | −66.67 | 50.00 |
| D 15 | −333.33 | −66.67 | 61.64 |
| D 20 | −433.33 | −33.33 | 75.00 |

TABLE 3-continued

Control Efficacy of Releasing *Stratiolaelaps scimitus* against Foliar-dwelling Thrips

| | Control | Release of *Stratiolaelaps scimitus* | |
|---|---|---|---|
| Time | Population reduction rate, % | Population reduction rate, % | Control efficacy, % |
| D 30 | −600.00 | −166.67 | 61.90 |
| D 40 | −800.00 | −233.33 | 62.96 |
| Average | −550.00 | −206.25 | 54.34 |

Note:
Population reduction rate = 100 × (Initial population density − Later population density)/Initial population density; Control efficacy = 100 × (Treated population reduction rate − Control population reduction rate)/(100 − Control population reduction rate)

As shown in Tables 2-3, the control efficacy against trap-monitored thrips ranged from 30% to 60%, with an average control efficacy of 50.82% (as shown in Table 2); and the control efficacy against foliar-dwelling thrips ranged from 30% to 80%, with an average control efficacy of 54.34% (as shown in Table 3), indicating that the method provides superior thrips control efficacy during tobacco seedling cultivation. Therefore, it can further prevent subsequent thrips-transmitted diseases and pests (including thrips and viruses transmitted thereby). The release of *Stratiolaelaps scimitus* according to this method exhibited superior control effects against both foliar-dwelling and trap-monitored thrips.

Example 2

It differed from Example 1 in that the removal of host plants of thrips was performed by spraying imidacloprid solution at a safe dosage.

Example 3

It differed from Example 1 in that the removal of host plants of thrips was performed by spraying acetamiprid solution at a safe dosage.

Although the present invention is described in detail with reference to the foregoing embodiments, those skilled in the art still can make modifications to technical solutions stated in the foregoing embodiments, or make equivalent replacements to some of the technical features described herein. Any modification, equivalent replacement, improvement, or the like made within the spirit and principle of the present invention should be included in the protection scope of the present invention.

What is claimed is:

1. A method for controlling thrips using *Stratiolaelaps scimitus* during float-tray-based tobacco seedling cultivation, comprising the following steps:

1) arranging a seedbed in a wind-sheltered sunny area with upwind positioning, and removing host plants of the thrips around the seedbed;

2) sowing 2 tobacco seeds per cell in float trays for the float-tray-based tobacco seedling cultivation, arranging 32 float trays per nursery greenhouse, placing the float trays in a nutrient solution tank, adding a formulated fertilizer solution for the float-tray-based tobacco seedling cultivation into the nutrient solution tank, arranging a plurality of nursery greenhouses in close proximity to form a nursery greenhouse cluster, erecting a plastic film vertically around the nursery greenhouse cluster, and arranging an insect-proof net around the nursery greenhouse cluster, and 3) after a rate of seedling emergence reaches over 90%, thinning seedlings, and on the following day, releasing the *Stratiolaelaps scimitus* into root soil of plants in the float trays at a rate of 4-12 mites per cell, followed by growing the seedlings until transplanting of the seedlings.

2. The method for controlling thrips using *Stratiolaelaps scimitus* during float-tray-based tobacco seedling cultivation of claim 1, wherein the step of thinning the seedlings is performed by retaining only one relatively healthy seedling per cell.

3. The method for controlling thrips using *Stratiolaelaps scimitus* during float-tray-based tobacco seedling cultivation of claim 1, wherein the step of removing the host plants of the thrips covers an area of at least 50 m around the nursery greenhouse cluster.

4. The method for controlling thrips using *Stratiolaelaps scimitus* during float-tray-based tobacco seedling cultivation of claim 1, wherein the step of erecting the plastic film vertically around the nursery greenhouse cluster uses a black or silver-black plastic film, with a bottom of the plastic film abutting against a ground surface.

5. The method for controlling thrips using *Stratiolaelaps scimitus* during float-tray-based tobacco seedling cultivation of claim 1, wherein the host plants of the thrips at least comprise: *Bidens pilosa, Capsicum annuum, Solanum melongena*, and various flowering ornamental plants.

6. The method for controlling thrips using *Stratiolaelaps scimitus* during float-tray-based tobacco seedling cultivation of claim 1, wherein a method for performing the step of removing the host plants of the thrips comprises manual removal and application of chemical pesticide reagents.

7. The method for controlling thrips using *Stratiolaelaps scimitus* during float-tray-based tobacco seedling cultivation of claim 6, wherein the application of chemical pesticide reagents comprises spraying at least one of spinetoram solution, imidacloprid solution, and acetamiprid solution at a safe dosage.

8. The method for controlling thrips using *Stratiolaelaps scimitus* during float-tray-based tobacco seedling cultivation of claim 1, wherein the step of removing the host plants of the thrips covers an area of 50-100 m around the nursery greenhouse cluster.

9. The method for controlling thrips using *Stratiolaelaps scimitus* during float-tray-based tobacco seedling cultivation of claim 1, wherein the step of removing the host plants of the thrips is performed 10 days before the step of sowing the tobacco seeds.

10. The method for controlling thrips using *Stratiolaelaps scimitus* during float-tray-based tobacco seedling cultivation of claim 1, wherein a preparation method of the formulated fertilizer solution for the float-tray-based tobacco seedling cultivation comprises: adding water into the nutrient solution tank; adding a formulated fertilizer for the float-tray-based tobacco seedling cultivation into the water; and then stirring for complete dissolution.

* * * * *